(12) United States Patent
Qin

(10) Patent No.: US 10,368,805 B2
(45) Date of Patent: Aug. 6, 2019

(54) ELECTRODE IMPEDANCE MEASUREMENT

(71) Applicant: Draeger Medical Systems, Inc., Andover, MA (US)

(72) Inventor: Derek Y. Qin, Andover, MA (US)

(73) Assignee: DRÄGERWERK AG & CO. KGAA, Lübeck (DE)

(*) Notice: Subject to any disclaimer, the term of this patent is extended or adjusted under 35 U.S.C. 154(b) by 440 days.

(21) Appl. No.: 15/394,349

(22) Filed: Dec. 29, 2016

(65) Prior Publication Data

US 2018/0184980 A1    Jul. 5, 2018

(51) Int. Cl.
| | |
|---|---|
| A61B 5/00 | (2006.01) |
| A61B 5/04 | (2006.01) |
| A61B 5/0428 | (2006.01) |
| A61B 5/0408 | (2006.01) |
| A61B 5/0205 | (2006.01) |
| A61B 5/053 | (2006.01) |

(52) U.S. Cl.
CPC .......... *A61B 5/6843* (2013.01); *A61B 5/0205* (2013.01); *A61B 5/04002* (2013.01); *A61B 5/04087* (2013.01); *A61B 5/04286* (2013.01); *A61B 5/053* (2013.01); *A61B 2562/0214* (2013.01)

(58) Field of Classification Search
CPC ............................ A61B 5/6843; A61B 5/0205
USPC ......................................................... 600/509
See application file for complete search history.

(56) References Cited

U.S. PATENT DOCUMENTS

| | | | |
|---|---|---|---|
| 4,417,590 A | 11/1983 | Smith et al. | |
| 4,577,639 A | 3/1986 | Simon et al. | |
| 4,598,281 A | 7/1986 | Mass | |
| 4,658,831 A | 4/1987 | Reinhard et al. | |
| 4,917,099 A | 4/1990 | Stice | |
| 5,704,351 A | 1/1998 | Mortara et al. | |
| 6,496,721 B1 | 12/2002 | Yonce | |

(Continued)

FOREIGN PATENT DOCUMENTS

| | | |
|---|---|---|
| EP | 0 571 075 A2 | 11/1993 |
| EP | 2 294 979 A1 | 3/2011 |

(Continued)

OTHER PUBLICATIONS

Calabria, "Understanding Lead-Off Detection in ECG," Texas Instruments Application Report SBAA196A—May 2012—Revised Jan. 2015, Texas Instruments Incorporation, retrieved on Feb. 2, 2015, 16 pages.

(Continued)

*Primary Examiner* — Nadia A Mahmood
(74) *Attorney, Agent, or Firm* — Wenderoth, Lind & Ponack, L.L.P.

(57) ABSTRACT

Systems and methods are provided herein for monitoring electrocardiogram (ECG) electrodes. Each ECG electrode is electrically connected to a patient body and a corresponding current source. A reference ECG electrode of the monitored ECG electrodes is selected. Current is injected into each electrode. Each current has a respective predetermined level. Based on the injected currents, ECG electrode voltages are generated. The injected currents are adjusted after measuring the ECG electrode voltages while the predetermined level through the reference ECG electrode is maintained. An impedance associated with each non-reference ECG electrode is determined based on the ECG electrode voltage and the injected current.

26 Claims, 4 Drawing Sheets

(56) References Cited

U.S. PATENT DOCUMENTS

| | | |
|---|---|---|
| 6,516,218 B1 | 2/2003 | Cheng et al. |
| 7,818,058 B2 | 10/2010 | Mentelos |
| 8,068,905 B2 | 11/2011 | Freeman et al. |
| 2002/0107435 A1 | 8/2002 | Swetlik et al. |
| 2003/0032989 A1 | 2/2003 | Herleikson |
| 2003/0083584 A1 | 5/2003 | Yonce |
| 2003/0163170 A1 | 8/2003 | Faisandier |
| 2004/0138540 A1 | 7/2004 | Baker et al. |
| 2006/0004295 A1 | 1/2006 | Prydekker |
| 2007/0038257 A1 | 2/2007 | Gray |
| 2008/0275316 A1 | 11/2008 | Fink et al. |
| 2010/0007413 A1 | 1/2010 | Herleikson |
| 2011/0213261 A1 | 9/2011 | Naware et al. |
| 2011/0270112 A1 | 11/2011 | Manera et al. |
| 2011/0295096 A1 | 12/2011 | Bibian et al. |
| 2011/0301665 A1 | 12/2011 | Mercanzini et al. |
| 2012/0065536 A1 | 3/2012 | Causevic et al. |
| 2015/0241505 A1 | 8/2015 | Freeman et al. |

FOREIGN PATENT DOCUMENTS

| | | |
|---|---|---|
| EP | 2 442 443 A1 | 4/2012 |
| EP | 2 465 426 A1 | 6/2012 |
| WO | 98/30145 A1 | 7/1998 |
| WO | 01/06923 A1 | 2/2001 |
| WO | 2006/050325 A2 | 5/2006 |
| WO | 2013074114 A1 | 5/2013 |
| WO | 2014021883 | 2/2014 |
| WO | 2014051590 | 4/2014 |
| WO | 2015153426 | 10/2015 |

OTHER PUBLICATIONS

International Search Report issued in PCT/US2012/049121, dated May 21, 2013.

ELECTRODE IMPEDANCE MEASUREMENT

TECHNICAL FIELD

The subject matter described herein relates generally to electrical circuits, and, more specifically, for measuring the contact impedance of an electrode to determine a connection quality associated with the electrode and a patient.

BACKGROUND

In the course of providing healthcare to patients, vital statistics and other patient parameters are monitored. Different types of patient monitoring devices are able to monitor physiological state of the patient via at least one electrode that is coupled to the skin of a patient at various locations on the body. For example, the electrical activity of the heart is routinely monitored in clinical environments using an electrocardiogram (ECG) monitor. The ECG monitor is connected to the patient by a plurality of electrodes that monitor the electrical impulses of the patient's heart. In order for the ECG monitor to effectively record the electrical impulses of a patient, electrodes extending therefrom conventionally include a conductive gel that is embedded in an adhesive pad used to secure the electrode to the body of a patient. Wires from the monitor are selectively connected to the electrode in order to communicate voltages detected to the ECG monitoring device to provide a healthcare practitioner with data regarding the patient's heart function.

The quality of the recorded signal depends on the electrical resistance between the electrode and the patient's body (i.e., patient skin). The resistance at the electrode-patient interface is known as contact impedance. Contact impedance can vary due to a number of factors such as electrode gel drying, skin moisture level, or loss of secure contact between an electrode and the patient's skin. Measurements to determine the contact impedance at various times while the patient is being monitored can ensure that the signal being monitored is of a sufficient quality.

SUMMARY

In one aspect, ECG electrodes are monitored in which each ECG electrode is electrically connected to a patient body and a corresponding current source. Each ECG electrode can be modeled by an offset voltage and a resistor. Positive current can be defined to flow from the ECG electrode to the patient body. A current is injected into each ECG electrode. Each current has a respective predetermined level. ECG electrode voltages generated by the injected currents are measured. After measurements are complete, a first reference ECG electrode of the monitored ECG electrodes is selected. The currents are then adjusted while maintaining the predetermined level through the first reference ECG electrode. Impedances corresponding to each non-reference ECG electrode of the ECG electrodes are determined based on the ECG electrode voltages and the injected currents.

In some variations, the impedances for signal characterization of the monitored ECG electrodes can be provided.

In other variations, the current sources can generate current of a magnitude less than or equal to two hundred nanoamperes. The current sources can also be a Direct Current (DC) sources. The adjusted currents can be at least one of opposite polarity of the injected currents, double magnitude of the injected currents, and zero. The adjusted currents can be maintained for a next calculation cycle.

In some variations, the impedance can be determined by generating a voltage equation, for each ECG electrode. The voltage equation can equate the ECG electrode voltage to a summation of a body voltage, an offset voltage of the ECG electrode, and a product of the current corresponding to the ECG electrode and the impedance. Values of the offset voltage of the ECG electrode, the body voltage, and the impedance can be unknown. The impedance, corresponding to each ECG electrode, can be determined by solving the generated voltages equations to cancel out the offset voltage of the ECG electrode and the body voltage.

In other variations, a second reference ECG electrode can be selected from the plurality of non-reference ECG electrodes. The first reference ECG electrode or the second reference ECG electrode can either be arbitrarily selected or selected to be an ECG electrode having a known impedance. The plurality of currents can be adjusted after measuring the plurality of ECG electrode voltages while maintaining the predetermined level through the second reference ECG electrode. Impedances corresponding to the first reference ECG electrode and the neutral drive electrode can be determined based on the plurality of ECG electrode voltages and the plurality of currents.

In some variations, systems can be provided for implementing various operations described herein that include at least one data processor, memory, and an electronic visual display for visually displaying vital signs or other physiological parameters of the patient. Such systems can form or otherwise comprise a patient monitor. In other variations, such systems can include the ECG electrodes.

The subject matter described herein provides many technical advantages. One technical advantage includes providing increased accuracy in impedance measurements by varying amplitudes of injected DC current to obtain multiple voltage measurements and combining those measurements to determine such impedance. By use of the method described herein, impedances can be determined without known values of offset voltages associated with the electrodes and body voltage values associated with injected currents.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

Lead-off detection is a feature of ECG monitoring which can introduce side effects such as loading down a differential amplitude input impedance, causing ECG segment distortion, and/or reducing neutral drive circuit operating ranges. A DC detection scheme can be implemented, for example, through the use of a pull-up/pull-down resistor or current source. A current source is an electronic circuit that delivers or absorbs electric current that is independent of the voltage across it. Using this scheme, the current level becomes small (i.e., nanoamperes). At this level, electrode offset voltage variation introduces measurement errors. Even with the traditional DC measurement scheme with a higher current level, the lead-off threshold has a large amount of variation. By varying current levels injected into each electrode lead and measuring the voltage across each electrode, a series of voltage equations can be developed and manipulated such that an impedance can be determined without known values of a body voltage associated with a patient or without known values of an electrode offset voltage of each ECG electrode.

Figure 1:
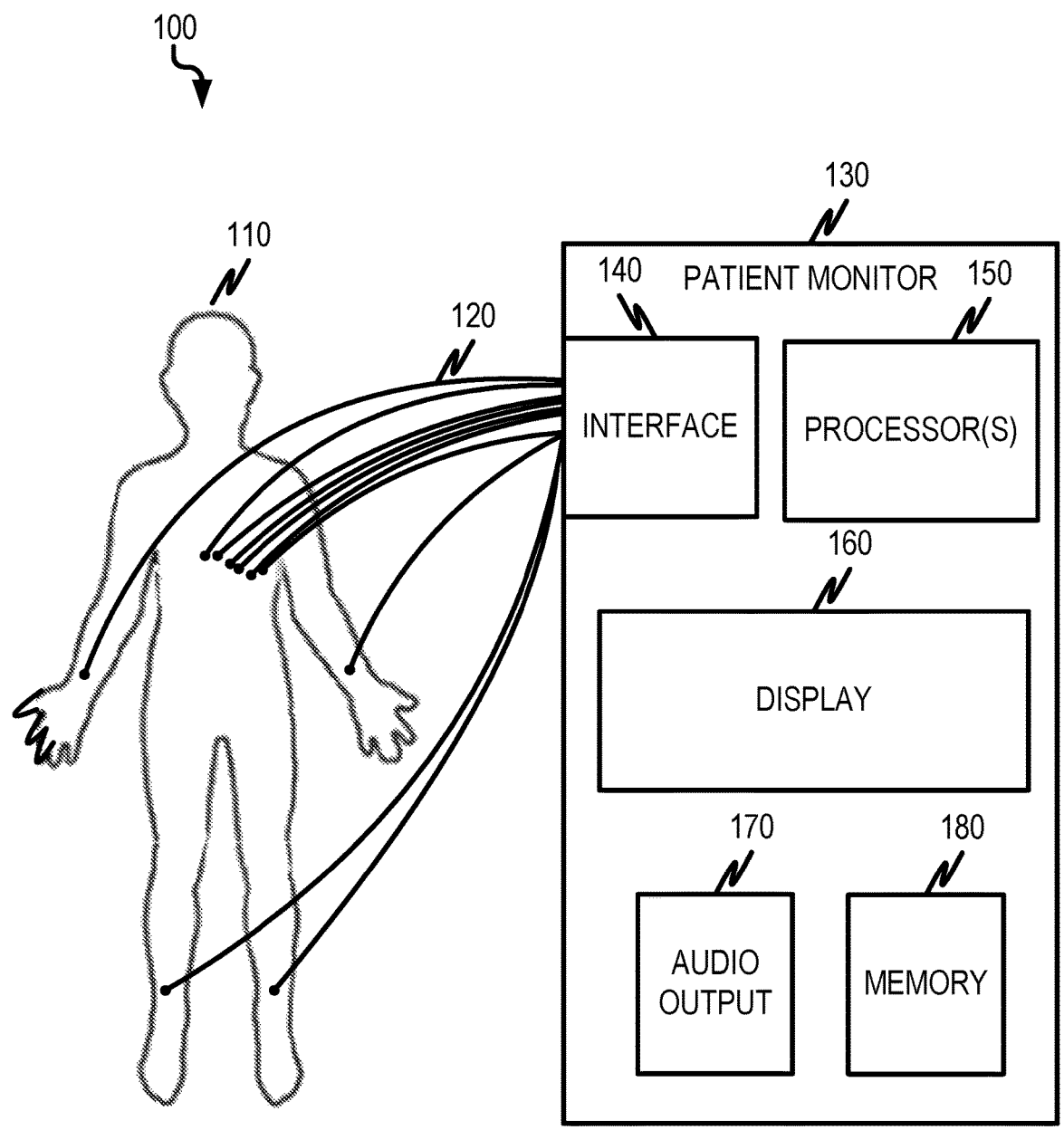
FIG. 1 is a diagram illustrating an example patient monitoring configuration for impedance measurements.

FIG. 1 is a diagram 100 illustrating an example patient monitoring configuration for impedance measurements. Patient monitor 130 can include memory 180 for storing instructions for execution by one or more processor/processor cores 150. Memory 180 can also be capable of storing data. The patient monitor 130 can include an electronic visual display 160 for rendering visual information that corresponds to the ECG data and patient vital signs (e.g., values, waveforms, etc.). In addition, the patient monitor 130 can also include an interface 140 that permits for wired or wireless communication with one or more electrodes of an electrode set 120 and/or a remote medical device and/or a remote computing system or network to transmit/receive data pertaining to ECG data and the like. In some variations, electrode set 120 can include, for example, a right arm electrode, a left arm electrode, and a left leg electrode. Patient monitor 130 can transmit data characterizing the ECG data of the patient 110 to a remote computing system (e.g., medical device, back-end computing system, etc.) via the interface 140. Patient monitor 130 can also include an audible alarm that can sound from an audio output 170 alerting a patient and/or medical staff.

Figure 2:
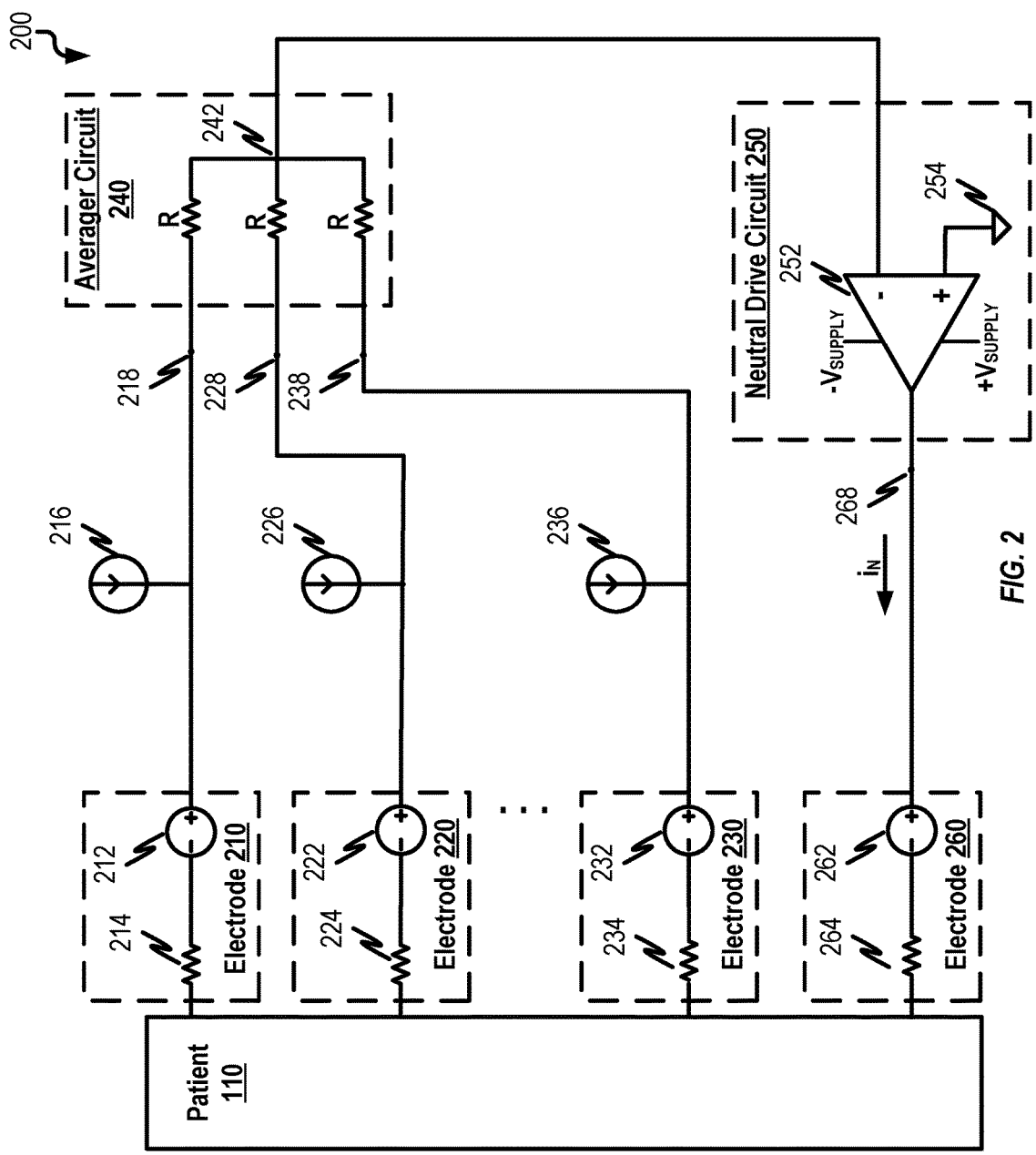
FIG. 2 is an example circuit diagram of electrodes affixed to a patient for measuring contact impedance.

FIG. 2 is an example circuit diagram 200 of electrodes affixed to a patient for measuring contact impedance. A number of electrodes (e.g., electrodes 210, 220, 230, 260) from electrode set 120 are affixed to patient 110. The number of electrodes can be dependent upon the type of monitoring being performed on patient 110. Current sources (e.g., current sources 216, 226, 236) can be electrically coupled to each electrode and controlled to inject a current into each corresponding electrode. Electrode 210 can be electrically coupled to current source 216. Electrode 220 can be electrically coupled to current source 226. Electrode 230 can be electrically coupled to current source 236. Current sources 216, 226, 236 can be DC current sources. Some electrodes (e.g., electrodes 210, 220, 230) can be electrically coupled to an averager circuit 240.

Averager circuit 240 can be patterned on a printed circuit board and can include resistors R electrically coupled to each electrode (i.e., electrodes 210, 220, 230) and can provide an average voltage across electrodes 210, 220, 230 at voltage point 242 such as a Wilson average voltage as described in WO 2015/153426, filed Mar. 30, 2015, entitled "Detecting Saturation in an Electrocardiogram Neutral Drive Amplifier," the entire contents of which are incorporated by reference herein. Resistors R can each be of a value ranging from 10 to 100 kΩ.

An output of averager circuit 240 can be electrically coupled to an inverting input of operational amplifier 252 of neutral drive circuit 250. Neutral drive circuit 250 can also be patterned on a printed circuit board. A signal ground 254 can be electrically coupled to a non-inverting input of operational amplifier 252. Operational amplifier 252 can be powered by a low voltage such as 1.5 V (i.e., $V_{SUPPLY}$). An output of operational amplifier 252 can be electrically coupled to a neutral drive electrode (i.e., electrode 260).

Each electrode can be modeled by an offset voltage source and a resistor electrically coupled in series. Electrode 210 can be represented by offset voltage source 212 and resistor 214. Electrode 220 can be represented by offset voltage source 222 and resistor 224. Electrode 230 can be represented by offset voltage 232 and resistor 234. A designated neutral drive electrode (i.e., electrode 260) can be represented by offset voltage source 262 and resistor 264. Positive current can be designated as flowing from each electrode to the patient 110. The offset voltage sources 212, 222, 232, 262 can be DC voltage sources. Resistors 214, 224, 234, 264 can be the combined resistances associated with patient 110 and each corresponding electrode 210, 220, 230, 264, respectively.

4 ECG Electrode Configuration

In one example, electrodes can be placed in various positions on patient 110. For example, electrode 210 can be positioned on a right arm (RA), electrode 220 can be positioned on a left arm (LA), electrode 230 can be positioned on left leg (LL), and neutral drive electrode (i.e., electrode 260) can be positioned on a right leg (RL). With this characterization, voltages as voltage points 218, 228, 238 can be represented as the summation of series voltages by:

$$V_{x\_RA}=V_B+V_{OS_{RA}}+i_{x_{RA}}R_{RA}, \quad (1)$$

$$V_{x\_LA}=V_B+V_{OS_{LA}}+i_{x_{LA}}R_{LA}, \text{ and} \quad (2)$$

$$V_{x\_LL}=V_B+V_{OS_{LL}}+i_{x_{LL}}R_{LL}, \quad (3)$$

where:
$V_x$ is a voltage measured at voltage points 218, 228, 238 for RA, LA, and LL, respectively, $V_B$ is a body voltage associated with patient 110, $V_{OS}$ is an offset voltage of offset voltage sources 212, 222, 232 for RA, LA, and LL, respectively, $i_x$ is current source 216, 226, 236 for RA, LA, and LL, respectively, and R is resistor 214, 224, 234 for RA, LA, and LL, respectively.

Offset voltages, $V_{OS}$, of offset voltage sources 212, 222, 232 are unknown and can vary in a range between −300 mV and +300 mV. Body voltage $V_B$ of patient 110 and resistance values of resistors 214, 224, 234 are unknown in Equations (1)-(3).

While current is injected into and sinked from electrodes 216, 226, 236 (i.e., current sources 216, 226, 236), the voltages at voltage points 218, 228, 238 can be measured. Current values for current sources 216, 226, 236 can be chosen individually in a hardware implementation controlled by either firmware and/or software. The firmware and/or software can reside in memory 180 or processor 150 of patient monitor 130. Current sources 216, 226, 236 can be set to inject currents on a range spanning −200 nanoamperes to +200 nanoamperes.

For example, a first set of currents can be injected using current source 216, 226, 236 as follows:

$$i_{x_{RA}}^{(1)}=i_0, \quad (4)$$

$$i_{x_{LA}}^{(1)}=-i_0, \text{ and} \quad (5)$$

$$i_{x_{LL}}^{(1)}=i_0. \quad (6)$$

In this example, $i_0$ is a current value controlled by the current source configurations. The difference in polarity of current sources 216, 226, 236 can minimize the current fed into the neutral drive electrode (i.e., electrode 260).

Using the injected current values a first set of voltage equations can be determined through substitution of Equations (4), (5), and (6) into Equations (1), (2), and (3), respectively resulting in:

$$V_{x_{RA}}^{(1)} = V_B^{(1)} + V_{OS_{RA}} + i_0 R_{RA}, \quad (7)$$

$$V_{x_{LA}}^{(1)} = V_B^{(1)} + V_{OS_{LA}} - i_0 R_{LA}, \text{ and} \quad (8)$$

$$V_{x_{LL}}^{(1)} = V_B^{(1)} + V_{OS_{LL}} + i_0 R_{LL}. \quad (9)$$

Voltage measurements can be taken at voltage points 218, 228, 238 and provide for known values for each electrode annotated by $V_x^{(1)}$ in Equations (7)-(9). The body voltage of patient 110 is dependent upon the injected first set of currents and is annotated as $V_B^{(1)}$.

After measuring the voltages at voltage points 218, 228, 238, the values for body voltage $V_B^{(1)}$, electrode offset voltages for each electrode $V_{OS}$, and resistances for each electrode, R, are unknown.

Resistors 214, 224 can be determined by selecting a reference ECG electrode (i.e., electrode 230) with a corresponding current source that is kept constant while adjusting current values to all other current sources. A second set of voltage measurements can be taken after adjusting the injected current values. For example, electrode 230 can be selected as a reference ECG electrode where the polarity and value of current source 236 are maintained. In this example, the polarity of current source 216 and current source 226 can be reversed. The adjusted injected current values include:

$$i_{x_{RA}}^{(2)} = -i_0, \quad (10)$$

$$i_{x_{LA}}^{(2)} = i_0, \text{ and} \quad (11)$$

$$i_{x_{LL}}^{(2)} = i_0. \quad (12)$$

A second set of voltage equations can be determined using the adjusted injected current values by substituting Equations (10), (11), and (12) into Equations (1), (2), and (3), respectively result in:

$$V_{x_{RA}}^{(2)} = V_B^{(2)} + V_{OS_{RA}} - i_0 R_{RA}, \quad (13)$$

$$V_{x_{LA}}^{(2)} = V_B^{(2)} + V_{OS_{LA}} + i_0 R_{LA}, \text{ and} \quad (14)$$

$$V_{x_{LL}}^{(2)} = V_B^{(2)} + V_{OS_{LL}} + i_0 R_{LL}. \quad (15)$$

Voltage measurements at voltage points 218, 228, 238 provide known voltage values for each electrode corresponding to the second set of adjusted currents as annotated by $V_x^{(2)}$. The body voltage of patient 110 depends upon the second set of injected currents and is annotated as $V_B^{(2)}$.

With the measured voltages at voltage points 218, 228, 238 and controlled current values, the values of $V_x$ and $i_0$ are known for each electrode in Equations (13), (14), and (15). The values $V_B^{(2)}$, $V_{OS}$, and R for each electrode are unknown.

Between the first set of injected currents and second set of adjusted injected currents, the offset voltages, $V_{OS}$, and resistances, R, for each electrode maintain the same unknown values as the physical electrode remains unchanged throughout the measurements. The resistances, R, for each electrode can be determined through mathematical relationships of various voltage equations. For example, taking the difference between Equation (15) and Equation (9), which corresponds to the reference ECG electrode selected, results in:

$$V_{x_{LL}}^{(2)} - V_{x_{LL}}^{(1)} = V_B^{(2)} - V_B^{(1)}. \quad (16)$$

Taking the difference between Equation (13) and Equation (7) results in:

$$V_{x_{RA}}^{(2)} - V_{x_{RA}}^{(1)} = V_B^{(2)} - V_B^{(1)} - 2i_0 R_{RA}, \quad (17)$$

where the resistance for $R_{RA}$ (i.e., resistor 214) can be determined by:

$$R_{RA} = \frac{[V_B^{(2)} - V_B^{(1)}] - [V_{x_{RA}}^{(2)} - V_{x_{RA}}^{(1)}]}{2i_0}. \quad (18)$$

As the body voltage is unknown in Equation (18), Equation (18) can be rewritten in terms of known voltage parameters by the substitution of Equation (16) into Equation (17) which results in:

$$R_{RA} = \frac{[V_{x_{LL}}^{(2)} - V_{x_{LL}}^{(1)}] - [V_{x_{RA}}^{(2)} - V_{x_{RA}}^{(1)}]}{2i_0}. \quad (19)$$

Similarly, resistance $R_{LA}$ (i.e., resistor 224) can be determined by first taking the difference between Equation (14) and Equation (8) to result in:

$$V_{x_{LA}}^{(2)} - V_{x_{LA}}^{(1)} = V_B^{(2)} - V_B^{(1)} + 2i_0 R_{LA} \quad (20)$$

where the resistance for $R_{LA}$ (i.e., resistor 224) can be determined by:

$$R_{LA} = \frac{[V_B^{(2)} - V_B^{(1)}] - [V_{x_{LA}}^{(2)} - V_{x_{LA}}^{(1)}]}{-2i_0}. \quad (21)$$

The unknown body voltage relationship can be eliminated from Equation (21) and rewritten in terms of known voltage variables by substituting Equation (16) into Equation (21) resulting in:

$$R_{LA} = \frac{[V_{x_{LL}}^{(2)} - V_{x_{LL}}^{(1)}] - [V_{x_{LA}}^{(2)} - V_{x_{LA}}^{(1)}]}{-2i_0} \quad (22)$$

The current output of neutral drive circuit 250 can be represented as:

$$i_N = -(i_{x_{RA}} + i_{x_{LA}} + i_{x_{LL}}). \quad (23)$$

The output current of neutral drive circuit 250, $i_N$, associated with the second set of adjusted currents can be determined by substituting Equations (10), (11), and (12) into Equation (23), the current through neutral drive circuit 250, $i_N$, is determined to be:

$$i_N^{(2)} = -i_0. \quad (24)$$

Using Equation (24), a representative voltage equation can be determined for the neutral drive electrode (i.e., electrode 260) as follows:

$$V_{x_{RL}}^{(2)} = V_B^{(2)} + V_{OS_{RL}} - i_0 R_{RL}. \quad (25)$$

In order to determine the resistances $R_{LL}$ (i.e., resistor 234) and $R_{RL}$ (i.e., resistor 264), the polarity of the current source corresponding to the selected reference ECG electrode 230 (i.e., current source 236) can be adjusted to provide a current of the opposite polarity such that a third set of currents are injected into current sources 216, 226, 236 as follows:

$$i_{x_{RA}}^{(3)} = -i_0, \tag{26}$$

$$i_{x_{LA}}^{(3)} = i_0, \text{ and} \tag{27}$$

$$i_{x_{LL}}^{(3)} = -i_0. \tag{28}$$

where the polarity and value of current for electrode 210 (i.e., RA electrode) or electrode 220 (i.e., LA electrode) is maintained. Either electrode 210 (i.e., RA electrode) or electrode 220 (i.e., LA electrode), or a combination of the two electrodes, can be selected as a reference ECG electrode for determining the impedance of electrode 230 (i.e., LL electrode) or electrode 260 (i.e., RL electrode). Through substitution of Equations (26), (27), and (28) into Equation (23), the current output of neutral drive circuit 250, $i_N$, corresponding to the third set of currents is:

$$i_N^{(3)} = i_0. \tag{29}$$

The voltages at voltage points 218, 228, 238, 268 can be measured. With the adjusted current values, a third set of representative voltage equations can be determined by substituting Equations (26), (27), (28) into Equations (1), (2), and (3), respectively resulting in:

$$V_{x_{RA}}^{(3)} = V_B^{(3)} + V_{OS_{RA}} - i_0 R_{RA}, \tag{30}$$

$$V_{x_{LA}}^{(3)} = V_B^{(3)} + V_{OS_{LA}} + i_0 R_{LA}, \text{ and} \tag{31}$$

$$V_{x_{LL}}^{(3)} = V_B^{(3)} + V_{OS_{LL}} - i_0 R_{LL}. \tag{32}$$

Additionally, the voltages associated with neutral drive electrode (i.e., electrode 260) can be represented by:

$$V_{x_{RL}}^{(3)} = V_B^{(3)} + V_{OS_{RL}} - i_0 R_{RL}. \tag{33}$$

In order to determine the resistance values, a series of differences can be taken with the representative voltage equations. The difference between Equation (30) and Equation (13) results in:

$$V_{x_{RA}}^{(3)} - V_{x_{RA}}^{(2)} = V_B^{(3)} - V_B^{(2)}. \tag{34}$$

Taking the difference between Equation (31) and Equation (14) results in:

$$V_{x_{LA}}^{(3)} - V_{x_{LA}}^{(2)} = V_B^{(3)} - V_B^{(2)} \tag{35}$$

Taking the difference between Equation (32) and Equation (15) results in:

$$V_{x_{LL}}^{(3)} - V_{x_{LL}}^{(2)} = V_B^{(3)} - V_B^{(2)} - 2i_0 R_{LL} \tag{36}$$

In order to eliminate the unknown body voltage values and to substitute in known voltage measurement values, a reference ECG electrode is selected. For example, the RA electrode (i.e., electrode 210) can be selected as the reference ECG electrode. With this selection, Equation (34) can be substituted into Equation (36) resulting in:

$$V_{x_{LL}}^{(3)} - V_{x_{LL}}^{(2)} = V_{x_{RA}}^{(3)} - V_{x_{RA}}^{(2)} - 2i_0 R_{LL}, \tag{37}$$

where the resistance for $R_{LL}$ (i.e., resistor 234) can be determined by:

$$R_{LL} = \frac{[V_{x_{LL}}^{(3)} - V_{x_{LL}}^{(2)}] - [V_{x_{RA}}^{(3)} - V_{x_{RA}}^{(2)}]}{-2i_0}. \tag{38}$$

Alternatively, the LA electrode (i.e., electrode 220) can be selected as the reference ECG electrode. With this selection, Equation (35) can be substituted into Equation (36) resulting in:

$$V_{x_{LL}}^{(3)} - V_{x_{LL}}^{(2)} = V_{x_{LA}}^{(3)} - V_{x_{LA}}^{(2)} - 2i_0 R_{LL}, \tag{39}$$

where the resistance for $R_{LL}$ (i.e., resistor 234) can be determined by:

$$R_{LL} = \frac{[V_{x_{LL}}^{(3)} - V_{x_{LL}}^{(2)}] - [V_{x_{LA}}^{(3)} - V_{x_{LA}}^{(2)}]}{-2i_0}. \tag{40}$$

In another example, both the RA electrode (i.e., electrode 210) and the LA electrode (i.e., electrode 220) can be selected together as the reference ECG electrode. The average of Equation (34) and Equation (35) can be substituted into Equation (36) resulting in:

$$V_{x_{LL}}^{(3)} - V_{x_{LL}}^{(2)} = \left(\frac{(V_{x_{RA}}^{(3)} - V_{x_{RA}}^{(2)}) + (V_{x_{LA}}^{(3)} - V_{x_{LA}}^{(2)})}{2}\right) - 2i_0 R_{LL}, \tag{41}$$

where the resistance for $R_{LL}$ (i.e., resistor 234) can be determined by:

$$R_{LL} = \frac{[V_{x_{LL}}^{(3)} - V_{x_{LL}}^{(2)}] - \left(\frac{(V_{x_{RA}}^{(3)} - V_{x_{RA}}^{(2)}) + (V_{x_{LA}}^{(3)} - V_{x_{LA}}^{(2)})}{2}\right)}{-2i_0}. \tag{42}$$

Similarly, resistance $R_{RL}$ (i.e., resistor 264) can be determined by first taking the difference between Equation (35) and Equation (25) to result in:

$$V_{x_{RL}}^{(3)} - V_{x_{RL}}^{(2)} = V_B^{(3)} - V_B^{(2)} + 2i_0 R_{RL} \tag{43}$$

In order to replace unknown values with known values, Equation (34) can be substituted into Equation (43) results in:

$$V_{x_{RL}}^{(3)} - V_{x_{RL}}^{(2)} = V_{x_{RA}}^{(3)} - V_{x_{RA}}^{(2)} + 2i_0 R_{LL} \tag{44}$$

where the resistance for $R_{RL}$ (i.e., resistor 264) can be determined by:

$$R_{RL} = \frac{[V_{x_{RL}}^{(3)} - V_{x_{RL}}^{(2)}] - [V_{x_{RA}}^{(3)} - V_{x_{RA}}^{(2)}]}{2i_0}. \tag{45}$$

The resistances $R_{RA}$ (i.e., resistor 214), $R_{LA}$ (i.e., resistor 224), $R_{LL}$ (i.e., resistor 234), and $R_{RL}$ (i.e., resistor 264) can be determined without knowing the body voltage values, $V_B$, and offset voltages, $V_{OS}$, for each electrode (i.e., offset voltage sources 212, 222, 232, 262).

N-ECG Electrode Configuration

Values of N electrodes can be determined in a similar manner as the 4-electrode configuration example described herein. The positive direction of current can be defined as the direction from resistors, $R_i$, to patient 110, where $x_i$ designates an electrode and $V_{x_i}$ represents a voltage at the corresponding voltage point of the electrode resulting in the following, where N=10:

RL: $V_B + V_{OS_0} + i_{x_0} R_0 = V_{x_0}$ \hfill (46)

RA: $V_B + V_{OS_1} + i_{x_1} R_1 = V_{x_1}$ \hfill (47)

LL: $V_B + V_{OS_2} + i_{x_2} R_2 = V_{x_2}$ \hfill (48)

LA: $V_B + V_{OS_3} + i_{x_3} R_3 = V_{x_3}$ \hfill (49)

$V_1: V_B+V_{OS_4}+i_{x_4}R_4=V_{x_4}$ (50)

$V_2: V_B+V_{OS_5}+i_{x_5}R_5=V_{x_5}$ (51)

$V_3: V_B+V_{OS_6}+i_{x_6}R_6=V_{x_6}$ (52)

$V_4: V_B+V_{OS_7}+i_{x_7}R_7=V_{x_7}$ (53)

$V_5: V_B+V_{OS_8}+i_{x_8}R_8=V_{x_8}$ (54)

$V_6: V_B+V_{OS_9}+i_{x_9}R_9=V_{x_9}$ (55)

for all values of i ranging between:

$i=0,1,2,\ldots N-1$ (56)

where the neutral drive current source is calculated to be $i_{x_0}^{(1)}=-\Sigma_{i=1}^{N-1}i_{x_1}^{(1)}$ (57)

and where the current values $i_{x_i}$, where i corresponds to the electrode.

In this example, the current sources can be initially set as follows:

$i_{x_i}=(-1)^i i_{src}$ and (58)

$i_{x_0}=-\Sigma_{i=1}^{N-1}i_{x_i}.$ (59)

where $i_{src}$ is a current value set for each corresponding current sources to each electrode. The corresponding voltage point values, $V_{x_i}$, can be measured at each voltage point corresponding to the electrode.

Voltages, $V_{x_i}$, can be measured at corresponding voltage points for each electrode determined to be in the "on" state and recorded as $V_{x_i}^{(1)}$. Among the connected electrodes, an electrode can be selected as a reference ECG electrode, $x_k$, such that the corresponding current source remains unchanged in terms of current direction and magnitude.

Reference ECG electrode, $x_k$, for example, can be selected arbitrarily or satisfying:

$V_{x_k}=\min(|V_{x_i}|).$ (60)

The current value of the current sources can be adjusted for the other electrodes while maintaining the current value of the current source corresponding to the reference ECG electrode, $x_k$. One way to adjust the current values for the other current sources can be achieved by flipping the current source polarity or by increasing the magnitude of current from the current source. Alternatively, the current sources can be set to zero. The corresponding voltages, $V_{x_i}$, can be measured at the voltage points for each electrode and recorded as $V_{x_i}^{(2)}$. The resistances, $R_i$, for each electrode can be determined for each electrode by:

$$R_i = \frac{\Delta V_{x_i} - \Delta V_{x_k}}{\Delta i_{x_i}},$$ (61)

where $i \neq j \neq k \neq 0,$ (62)

$\Delta i_{x_i}=i_{x_i}^{(2)}-i_{x_i}^{(1)},$ (63)

$\Delta V_{x_k}=V_{x_k}^{(2)}-V_{x_k}^{(1)},$ and (64)

$\Delta V_{x_i}=V_{x_i}^{(2)}-V_{x_i}^{(1)}.$ (65)

Among the electrodes having a known, calculated resistance value $R_i$, another electrode can be selected as the reference ECG electrode, $x_r$, such that the current value of the corresponding current source is maintained while the other DC current sources are modified, including the current source corresponding to $x_k$. The neutral drive current source can be calculated to be:

$i_{x_0}^{(3)}=-\Sigma_{i=1}^{N-1}i_{x_i}^{(3)},$ (66)

Voltages, $V_{x_i}$, can be measured at the voltage points for each electrode and recorded as $V_{x_i}^{(3)}$ where the corresponding resistances, $R_i$, can be determined for each electrode by:

$$R_k = \frac{\Delta V_{x_k} - \Delta V_{x_r}}{\Delta i_{x_k}} \text{ and}$$ (67)

$$R_0 = \frac{\Delta V_{x_0} - \Delta V_{x_r}}{\Delta i_{x_0}},$$ (68)

where $\Delta i_{x_k}=i_{x_k}^{(3)}-i_{x_k}^{(2)},$ (69)

$\Delta V_{x_k}=V_{x_k}^{(3)}-V_{x_k}^{(2)},$ (70)

$\Delta V_{x_0}=V_{x_0}^{(3)}-V_{x_0}^{(2)},$ (71)

$\Delta i_{x_0}=i_{x_0}^{(3)}-i_{x_0}^{(2)},$ and (72)

$\Delta V_{x_r}=V_{x_r}^{(3)}-V_{x_r}^{(2)}.$ (73)

Next, the current values of the current sources can be returned to the initial values as provided in Equations (58) and (59) until the next calculation cycle. Alternatively, the current values of the DC current sources can be maintained at until the next calculation cycle.

The demonstrated examples cancel out the offset voltages, $V_{OS_i}$, and the body voltage, $V_B$, effects, offset voltage effects associated with neutral drive circuit 250 and/or leakage current effects associated with printed circuit boards containing neutral drive circuit 250 and/or ECG lead protection and filter networks. The current sources can be of small current values that provide for a wider neutral drive and ECG operating range. Extremely high impedance values also reduce the amount of distortion and improve cardiac magnetic resonance readings. The values of the electrode resistances, $R_i$, can be recorded corresponding to the electrode ECG manufacturers for future product improvements.

Figure 3:
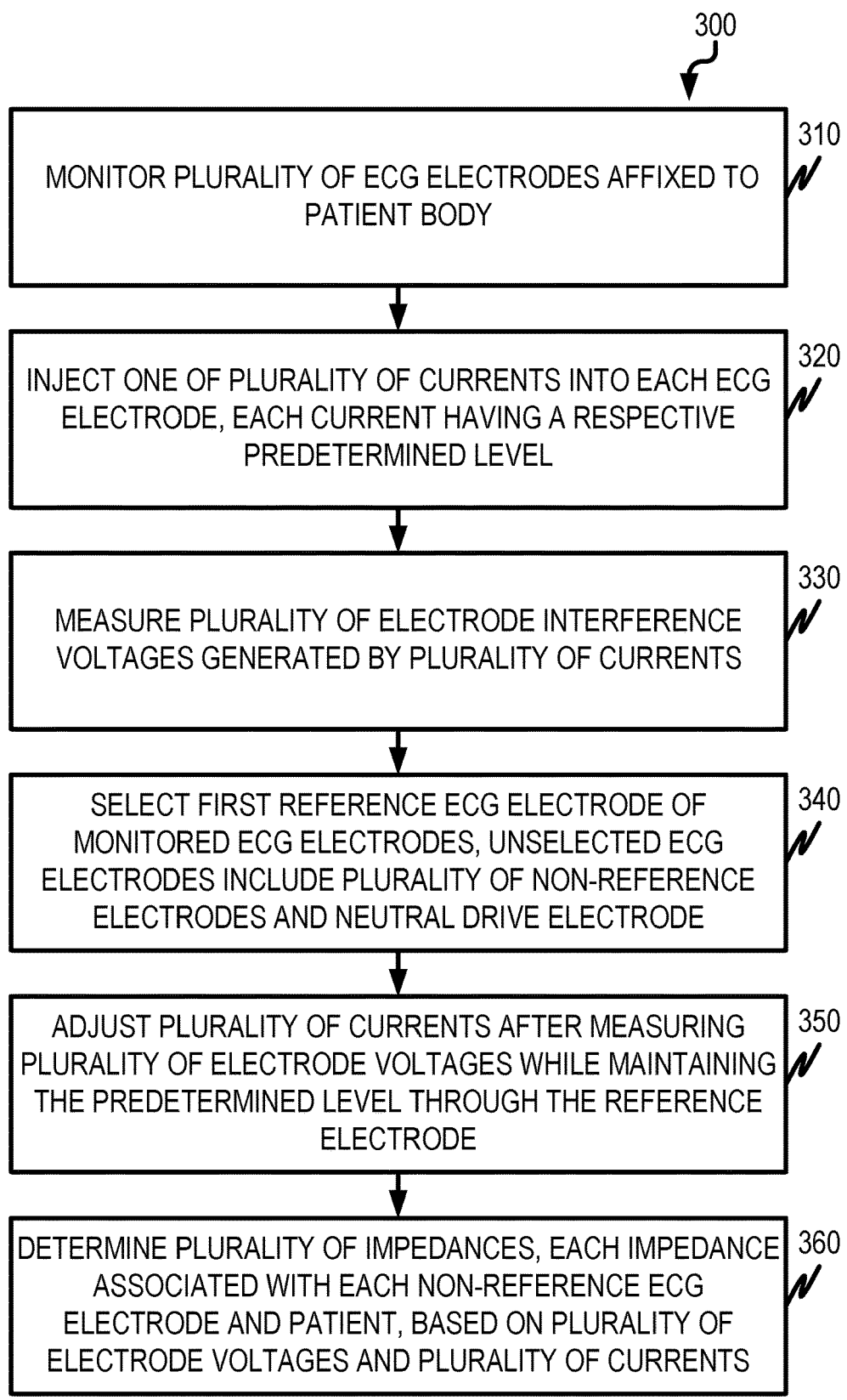
FIG. 3 is example process flow diagram for determining impedances associated with ECG electrodes.

FIG. 3 is example process flow diagram 300 for determining impedances associated with ECG electrodes. ECG electrodes, each electrically connected to a body of a patient, can be monitored, at 310. Each ECG electrode can be modeled by an offset voltage source and a resistor electrically coupled together in series. The resistor can be a combined resistance of patient 110 and the resistance associated with the corresponding ECG electrode. One of a plurality of currents can be injected, at 320, into each ECG electrode, each current having a respective predetermined level. A plurality of electrode voltages generated by the plurality of currents can be measured, at 330, at each respective electrode voltage point (i.e., voltage points 218, 228, 238). A reference ECG electrode of the monitored ECG electrodes can be selected, at 340. The ECG electrodes that are not selected include a neutral drive electrode and a plurality of non-reference ECG electrodes. After selecting a reference ECG electrode, the plurality of currents can be adjusted, at 350, while the predetermined level through the reference ECG electrode is maintained. A plurality of impedances, each impedance associated with each non-reference ECG electrode, can be determined, at 360, based on the plurality of electrode voltages and the plurality of currents.

The impedances associated with the reference ECG electrode and neutral drive electrode remain unknown.

Figure 4:
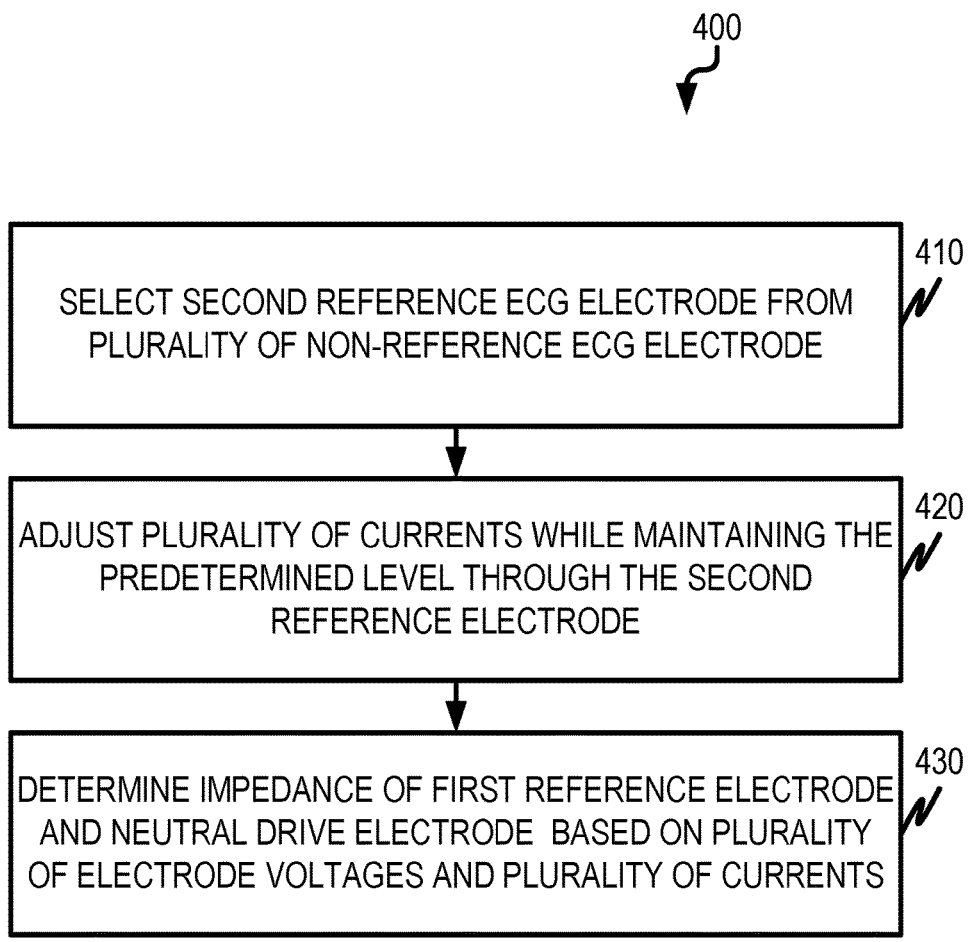
FIG. 4 is an example process flow diagram for determining impedances associated with the reference ECG electrode and the neutral drive electrode.

FIG. 4 is an example process flow diagram 400 for determining impedances associated with the reference ECG electrode (i.e., electrode 230) and the neutral drive electrode (i.e., electrode 260). A second reference ECG electrode (i.e., electrode 210 or electrode 220) can be selected, at 410, from the plurality of non-reference ECG electrodes. The plurality of currents can be adjusted, at 420, while maintaining the predetermined level through the second reference ECG electrode. The impedance corresponding to the reference ECG electrode and neutral feedback electrode can be determined, at 430, based on the plurality of electrode voltages and plurality of currents.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system can include clients and servers. A client and server are generally remote from each other and typically interact through a communication network. The relationship of client and server arises by virtue of computer programs running on the respective computers and having a client-server relationship to each other. The computing systems/devices can include a variety of devices including personal computers, mobile phones, tablet computers, and Internet-of-Things (IoT) devices.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "computer-readable medium" refers to any computer program product, apparatus and/or device, such as for example magnetic discs, optical disks, solid-state storage devices, memory, and Programmable Logic Devices (PLDs), used to provide machine instructions and/or data to a programmable data processor, including a computer-readable medium that receives machine instructions as a computer-readable signal. The term "computer-readable signal" refers to any signal used to provide machine instructions and/or data to a programmable data processor. The computer-readable medium can store such machine instructions non-transitorily, such as for example as would a non-transient solid-state memory or a magnetic hard drive or any equivalent storage medium. The computer-readable medium can alternatively or additionally store such machine instructions in a transient manner, for example, as would a processor cache or other random access memory associated with one or more physical processor cores.

To provide for interaction with a user, the subject matter described herein can be implemented on a computer having a display device (e.g., a CRT (cathode ray tube) or LCD (liquid crystal display) monitor) for displaying information to the user and a keyboard and a pointing device (e.g., a mouse or a trackball) and/or a touch-screen by which the user can provide input to the computer. Other kinds of devices can be used to provide for interaction with a user as well; for example, feedback provided to the user can be any form of sensory feedback (e.g., visual feedback, auditory feedback, and/or tactile feedback); and input from the user can be received in any form, including acoustic, speech, or tactile input.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method implemented by one or more data processors forming part of at least one computing device, the method comprising:

monitoring, by at least one data processor of a computing device, electrocardiogram (ECG) electrodes each electrically connected to a patient body and a corresponding current source;

injecting, by the at least one data processor, one of a plurality of currents, each current having a respective predetermined level, into each ECG electrode;

measuring, by the at least one data processor, a plurality of ECG electrode voltages generated by the plurality of currents;

selecting, by the at least one data processor, a first reference ECG electrode from the monitored ECG electrodes, wherein unselected ECG electrodes include a plurality of non-reference ECG electrodes and a neutral drive electrode;

adjusting, by the at least one data processor, the plurality of currents after measuring the plurality of ECG electrode voltages while maintaining the predetermined level through the first reference ECG electrode; and determining, by the at least one data processor, a plurality of impedances, each impedance corresponding to each non-reference ECG electrode, based on the plurality of ECG electrode voltages and the plurality of currents.

2. The method according to claim 1, further comprising:
selecting, by the at least one data processor, a second reference ECG electrode from the plurality of non-reference ECG electrodes;
adjusting, by the at least one data processor, the plurality of currents after measuring the plurality of ECG electrode voltages while maintaining the predetermined level through the second reference ECG electrode; and
determining, by the at least one data processor, impedances corresponding to the first reference ECG electrode and the neutral drive electrode based on the plurality of ECG electrode voltages and the plurality of currents.

3. The method according to claim 1, wherein each ECG electrode is modeled by an offset voltage and a resistor.

4. The method according to claim 3, wherein determining the plurality of impedances comprises:
generating, by the at least one data processor, a voltage equation, for each ECG electrode, by equating the ECG electrode voltage to a summation of a body voltage, the offset voltage, and a product of the current corresponding to the ECG electrode and the impedance, wherein values of the offset voltage, the body voltage, and the impedance are unknown; and
determining, by the at least one data processor, the impedance, for each ECG electrode, by solving the plurality of generated voltages equations to cancel out the offset voltage of the ECG electrode and the body voltage.

5. The method according to claim 1, wherein positive current flows from the ECG electrode to the patient body.

6. The method according to claim 1, wherein the adjusted plurality of currents is at least one of opposite polarity of the plurality of currents, double magnitude of the plurality of currents, and zero.

7. The method according to claim 1, wherein the current sources are Direct Current (DC) sources.

8. The method according to claim 1, wherein each of the plurality of current sources generate current of a magnitude less than or equal to two hundred nanoamperes.

9. The method according to claim 1, wherein the adjusted plurality of currents are maintained for a next calculation cycle.

10. The method according to claim 1, wherein the first reference ECG electrode or the second reference ECG electrode is either arbitrarily selected or selected to be an ECG electrode having a known impedance.

11. The method according to claim 1, further comprising providing the plurality of impedances for signal characterization of the monitored ECG electrodes.

12. A system comprising:
at least one data processor; and
memory storing instructions which, when executed by the at least one data processor, result in operations comprising:
monitoring electrocardiogram (ECG) electrodes each electrically connected to a patient body and a corresponding current source;
injecting one of a plurality of currents, each current having a respective predetermined level, into each ECG electrode;
measuring a plurality of ECG electrode voltages generated by the plurality of currents;
selecting a first reference ECG electrode from the monitored ECG electrodes, wherein unselected ECG electrodes include a plurality of non-reference ECG electrodes and a neutral drive electrode;
adjusting the plurality of currents after measuring the plurality of ECG electrode voltages while maintaining the respective predetermined level through the first reference ECG electrode; and
determining a plurality of impedances, each impedance corresponding to each non-reference ECG electrode, based on the plurality of ECG electrode voltages and the plurality of currents.

13. The system according to claim 12, wherein the operations further comprise:
selecting a second reference ECG electrode from the plurality of non-reference ECG electrodes;
adjusting the plurality of currents after measuring the plurality of ECG electrode voltages while maintaining the respective predetermined level through the second reference ECG electrode; and
determining impedances corresponding to the first reference ECG electrode and the neutral drive electrode based on the plurality of ECG electrode voltages and the plurality of currents.

14. The system according to claim 12, wherein the operations further comprise:
an electronic visual display for visually displaying vital signs of the patient body, wherein the non-transitory computer readable media and the electronic visual display form part of a patient monitor.

15. The system according to claim 12, further comprising the plurality of ECG electrodes.

16. The system according to claim 12, wherein each ECG electrode is modeled by an offset voltage and a resistor.

17. The system according to claim 16, wherein determining the plurality of impedances comprises:
generating a voltage equation, for each ECG electrode, by equating the ECG electrode voltage to a summation of a body voltage, an offset voltage of the ECG electrode, and a product of the current corresponding to the ECG electrode and the impedance, wherein values of the offset voltage of the ECG electrode, the body voltage, and the impedance are unknown; and
determining the impedance, corresponding to each non-reference ECG electrode, by solving the plurality of generated voltages equations to cancel out the offset voltage of the ECG electrode and the body voltage.

18. The system according to claim 12, wherein positive current flows from the electrode to the patient body.

19. The system according to claim 12, wherein the adjusted plurality of currents is at least one of opposite polarity of the plurality of currents, double magnitude of the plurality of currents, and zero.

20. The system according to claim 12, wherein the current sources are Direct Current (DC) sources.

21. The system according to claim 12, wherein each of the current sources generate current of a magnitude less than or equal to two hundred nanoamperes.

22. The system according to claim 12, wherein the adjusted plurality of current values are maintained for a next calculation cycle.

23. The system according to claim 12, wherein the first reference ECG electrode or the second reference ECG electrode is either arbitrarily selected or selected to be an ECG electrode having a known impedance.

24. The system according to claim 12, wherein the operations further comprise providing the plurality of impedances for signal characterization of the monitored ECG electrodes.

25. A computer programmable product comprising a computer-readable storage medium having computer-readable instructions stored in the computer-readable storage medium for executing the operations comprising:

monitoring electrocardiogram (ECG) electrodes each electrically connected to a patient body and a corresponding current source;

injecting one of a plurality of currents, each current having a respective predetermined level, into each ECG electrode;

measuring a plurality of ECG electrode voltages generated by the plurality of currents;

selecting a first reference ECG electrode from the monitored ECG electrodes, wherein unselected ECG electrodes include a plurality of non-reference ECG electrodes and a neutral drive electrode;

adjusting the plurality of currents after measuring the plurality of ECG electrode voltages while maintaining the predetermined level through the first reference ECG electrode; and determining a plurality of impedances, each impedance corresponding to each non-reference ECG electrode of the ECG electrodes, based on the plurality of ECG electrode voltages and the plurality of currents.

26. The computer programmable product according to claim 25, wherein the operations further comprise:

selecting a second reference ECG electrode from the plurality of non-reference ECG electrodes;

adjusting the plurality of currents after measuring the plurality of ECG electrode voltages while maintaining the predetermined level through the second reference ECG electrode; and determining impedances corresponding to the first reference ECG electrode and the neutral drive electrode based on the plurality of ECG electrode voltages and the plurality of currents.

* * * * *